(12) United States Patent
Fetz et al.

(10) Patent No.: US 6,393,893 B1
(45) Date of Patent: May 28, 2002

(54) MEASURING DEVICE AND METHOD FOR MEASURING GAS LOAD IN LIQUIDS, ESPECIALLY IN LIQUID PLASTIC MATERIALS

(75) Inventors: Dietmar Fetz, Lustenau; Hannes Hausbichler, Bregenz, both of (AT)

(73) Assignee: EDF Polymer Applikation Maschinenfabrik GmbH, Horbranz (AT)

( * ) Notice: Subject to any disclaimer, the term of this patent is extended or adjusted under 35 U.S.C. 154(b) by 0 days.

(21) Appl. No.: 09/462,794

(22) PCT Filed: Jul. 10, 1998

(86) PCT No.: PCT/EP98/04280

§ 371 (c)(1),
(2), (4) Date: Feb. 22, 2000

(87) PCT Pub. No.: WO99/02963

PCT Pub. Date: Jan. 21, 1999

(30) Foreign Application Priority Data

Jul. 11, 1997 (DE) .................................. 297 12 263 U

(51) Int. Cl.⁷ ....................... G01N 7/14; G01N 33/414; B29C 44/60
(52) U.S. Cl. ....................... 73/19.01; 73/19.05; 73/19.1
(58) Field of Search ....................... 73/19.01, 19.03, 73/19.05, 19.06, 19.1

(56) References Cited

U.S. PATENT DOCUMENTS

| | | |
|---|---|---|
| 3,673,853 A | 7/1972 | Griswold |
| 3,853,500 A | 12/1974 | Gassmann |
| 4,090,695 A | 5/1978 | Stone |
| 4,164,137 A * | 8/1979 | Williamson ................. 73/19.1 |
| 4,299,794 A | 11/1981 | Kelley |
| 4,376,172 A | 3/1983 | Belangee |
| 4,862,729 A | 9/1989 | Toda |
| 5,509,294 A * | 4/1996 | Gowing ..................... 73/19.05 |

FOREIGN PATENT DOCUMENTS

| | | | |
|---|---|---|---|
| DE | 33 36 037 | 4/1985 | |
| DE | 31 32 597 | 8/1985 | |
| DE | 37 20 904 | 3/1988 | |
| DE | 36 30 209A A1 | 5/1989 | |
| DE | 38 30 209 | 3/1990 | |
| DE | 41 19 966 | 1/1993 | |
| EP | 0 125 541 | 4/1984 | |
| EP | 0 516 904 | 12/1992 | ............ 73/19.1 |
| EP | 0 525 933 | 2/1993 | ............ 73/19.05 |
| JP | 60-201918 | 12/1985 | |
| WO | WO 92/08121 | 5/1992 | |

* cited by examiner

Primary Examiner—Daniel S. Larkin
(74) Attorney, Agent, or Firm—Vickers, Daniels & Young

(57) ABSTRACT

This invention relates to a measuring apparatus for measuring the gas loading of a liquid, comprising a measuring device which substantially consists of a piston pump, by means of which a sample quantity of the liquid is subjected to a reduced pressure in a measuring cylinder chamber and the dissolved amount of gas is thereby desorbed and can be determined via the gas law by changing the conditions of pressure and/or temperature in the cylinder chamber. The measuring apparatus is of particularly compact construction and for this purpose is provided with a servomotor as an actuating drive for the piston pump, which servomotor not only enables the reduced pressure to be generated in the measuring chamber but also ensures the return of the measured test sample from the measuring cylinder chamber after the measuring operation. Preferably, the measuring apparatus is provided with an ultrasonic generator by means of which the test sample is acoustically irradiated and the time of desorption for expelling the gas is thus considerably shortened.

36 Claims, 3 Drawing Sheets

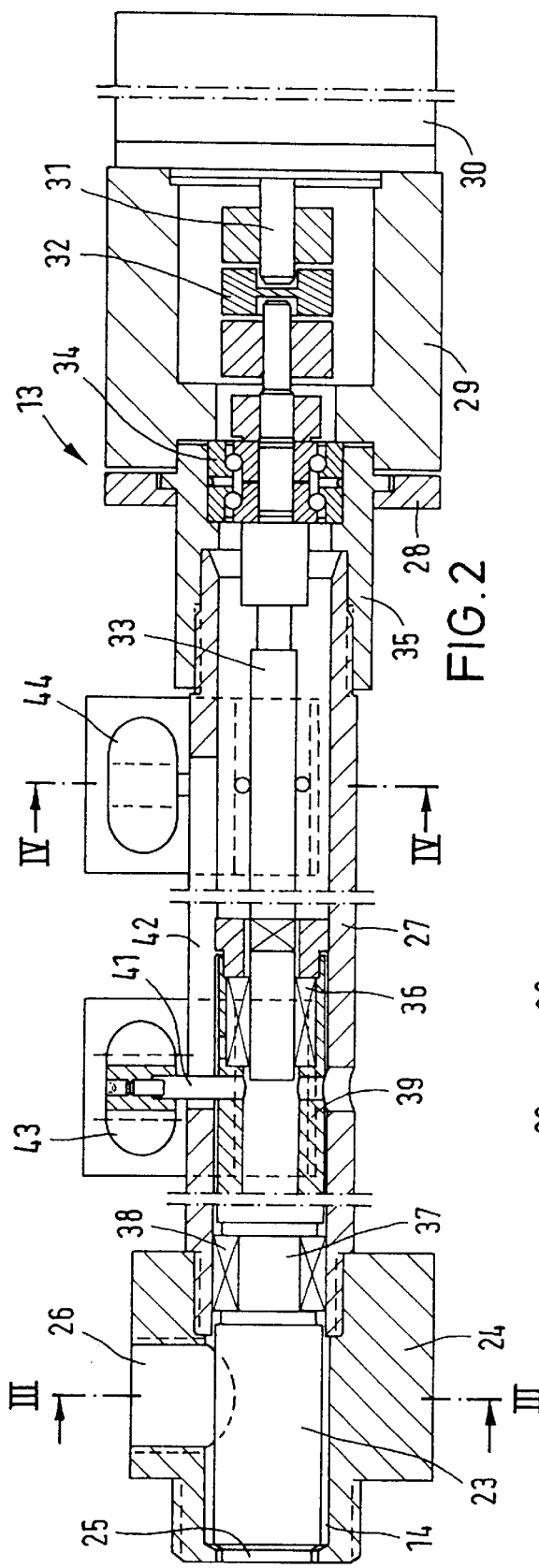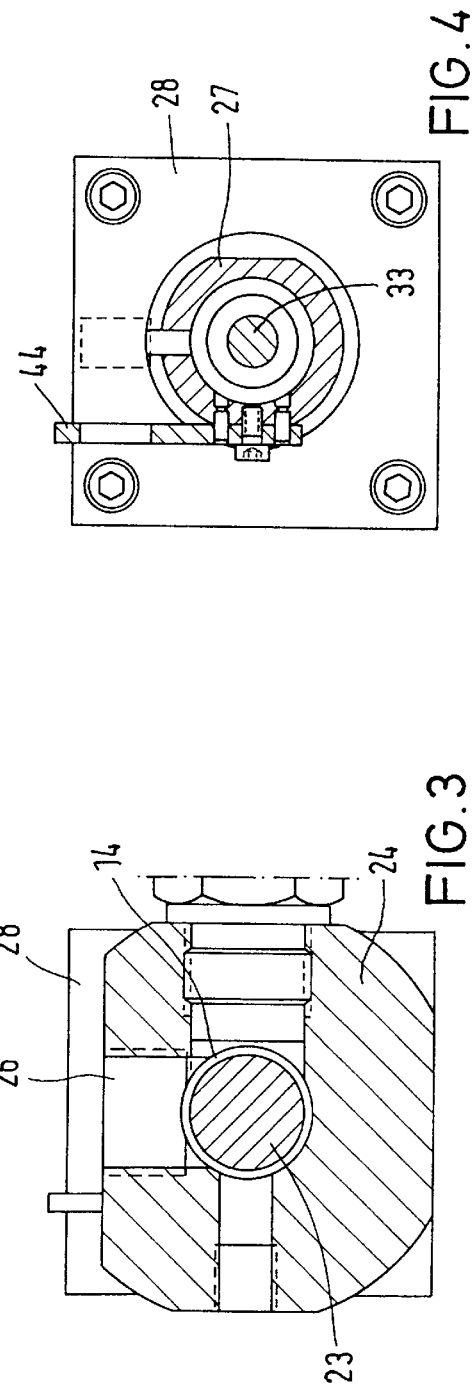

MEASURING DEVICE AND METHOD FOR MEASURING GAS LOAD IN LIQUIDS, ESPECIALLY IN LIQUID PLASTIC MATERIALS

FIELD OF THE INVENTION

This invention relates to a measuring apparatus for measuring the gas loading of a liquid, particularly of a liquid plastics component, comprising a pump which is disposed in a circuit for the sample quantity and the pump piston of which can be adjusted, with displacement control and by means of an actuating drive, in both directions of travel in the measuring cylinder chamber, comprising a switchable valve device forming a filling and ejection valve for filling the measuring cylinder chamber with the sample quantity to be measured and for carrying away the sample quantity from the measuring cylinder chamber after the measuring operation has been performed, and comprising a pressure measuring device which is associated with the measuring cylinder chamber and with which the pressure of the sample quantity, which is isolated in the measuring cylinder chamber when the valve device is closed, can be measured at different predetermined positions of displacement of the pump piston in order to determine the gas loading. The present invention is further oriented towards a method of determining the gas loading of a liquid, using the measuring apparatus according to the invention in particular.

BACKGROUND OF THE INVENTION

In technology, and above all in plastics processing technology, it is frequently necessary to measure the gas loading of liquids, e.g. the content of air of liquid plastics components for the production of foamed materials, generally with the aim of being able to operate with a constant gas loading in continuous operation.

Numerous measuring apparatuses have long been known for determining the gas loading of liquids, particularly of liquid plastics components (DE 37 20 904 A1, DE 33 36 037 A1, DE 31 32 597 C2, DE 36 30 209 A1, DE 41 19 966 A1, EP 0 125 541 A2). These known measuring apparatuses generally employ measuring cylinders which are provided with measuring pistons and into which a defined amount of sample is drawn off at intervals from the system conveying the gas-laden liquid. A measurement is then made on this sample, which is isolated from the system in the measuring cylinder. This is generally effected by subjecting the sample quantity, which is loaded with dissolved gas and possibly with free gas also, to a reduced pressure in the closed measuring cylinder chamber, with the release of the gas, by increasing the volume of the measuring cylinder chamber by correspondingly adjusting the piston. The gas loading of the liquid can be calculated from the changes in volume determined and from the changes in pressure of the sample quantity in accordance with known physical relationships (gas law). It is possible to achieve the same result if the measuring sample is measured in the measuring cylinder by compression by means of the measuring piston and/or by a combination of decompression and subsequent compression, with the measurement of pressure under the different test conditions and simultaneous determination of the volume of the measuring space for the different piston positions.

A measuring apparatus for measuring the gas loading of a liquid, particularly a liquid plastics component, comprising a pump which is disposed in a circuit for the sample quantity and the pump piston of which can be adjusted, with displacement control and by means of an actuating drive, in both directions of travel in the measuring cylinder chamber, comprising a switchable valve device forming a filling and ejection valve for filling the measuring cylinder chamber with the sample quantity to be measured and for carrying away the sample quantity from the measuring cylinder chamber after the measuring operation has been performed, and comprising a pressure measuring device which is associated with the measuring cylinder chamber and with which the pressure of the sample quantity, which is isolated in the measuring cylinder chamber when the valve device is closed, can be measured at different predetermined positions of displacement of the pump piston in order to determine the gas loading is known from U.S. Pat. No. 4,376,172. The measuring cylinder chamber of which is connected on its inlet side, via a filling valve, to the system which carries the gas-laden liquid under pressure and which comprises a supply vessel for the gas-laden liquid, and which is connected on its outlet side, via an ejection valve, to a return line which leads back to the supply vessel. Here also, the gas loading is measured by withdrawing a defined amount of sample from the system and feeding it to the measuring cylinder of the measuring pump, followed by making a measurement on the sample with the filling and ejection valves closed, namely with the sample isolated from the system, for which purpose firstly a reduced pressure and then an overpressure is generated in the measuring cylinder by adjusting the piston with control of the displacement thereof. In the course of this procedure, the measured pressure values, as well as the changes in volume of the measuring cylinder chamber which result from the displacement movements of the measuring piston, are processed by an electronic evaluation unit and are utilized for controlling the gas loading of the liquid at a predetermined constant value. After the measuring operation has been performed, the filling valve and the outlet valve are opened again, so that the test sample is returned to the supply vessel again by the pump pressure in the system. In the intervals between the periodic measurements made on samples, the measuring cylinder of the pump is always connected to the pumping system of the installation as a whole.

SUMMARY OF THE INVENTION

This invention stems from these known measuring apparatuses, and stems in particular from the apparatus which employs measuring pump according to the aforementioned U.S. Pat. No. 4,376,172. The object of the invention is primarily to fashion this system, particularly the piston pump which is used here as the measuring apparatus for gas loading, without an excessive cost of construction and so that an accurate measurement of the gas loading of liquids, particularly of liquid plastics components for the production of synthetic foam, can be achieved in different operating systems and with different arrangements of the piston pump.

This object is achieved according to the invention by providing the actuating drive of the piston pump as a controlled servomotor together with a transmission gear and by constructing the piston pump at the same time as a feed pump which returns the test sample from the measuring cylinder chamber to the system after the measuring operation has been performed.

With this design of measuring apparatus, and by means of the controlled servomotor and of the associated transmission gear, it is possible to make a very accurate adjustment of the displacement of the pump piston both in the direction of suction and in the direction of compression, and it is consequently possible to make an accurate determination of the change in volume of the measuring cylinder chamber which occurs during the measuring operation, so that the gas content of the test sample can be determined exactly via the displacement-dependent changes in volume and via the pressure values which are measured simultaneously. At the same time, the piston pump according to the invention can operate as a feed pump which pushes the test sample out of the pump cylinder forming the measuring cylinder chamber when the ejection valve is opened after the measurement has been made. Thus,it is also possible to locate the piston pump according to the invention in a separate circuit which is separated from the pumping system of the installation as a whole, and to shut off the measuring cylinder chamber of the piston pump from the pressurised system in the intervals between measuring operations. In this connection, valves which can be switched independently of each other from their closed position into their open position and vice versa are preferably used for the filling valve and the ejection valve which are associated with the piston pump, so that it is possible to fill the measuring cylinder chamber with the test sample, with the filling valve open and the ejection valve closed, and it is possible to eject the test sample after the measuring operation has been performed, with the filling valve closed and the ejection valve open.

In a further advantageous embodiment of the invention, the measuring apparatus which is associated with the piston pump is constructed so that it measures both the pressure of the test sample at different volumes of the measuring cylinder chamber and the temperature of the test sample. The effect of temperature on the gas absorption behavior of the liquid can thereby also be measured metrologically and can be evaluated, e.g. to achieve constant gas loading of the liquid in operation.

Different drive components can be used both for the actuating drive and for the transmission gear of the piston pump according to the invention. A torque motor, the direction of rotation of which can be reversed, preferably an electric torque motor in the form of a stepper motor, can advantageously be used for the servomotor. One advantageous embodiment of the transmission gear consists of a spindle gear, to the axially displaceable spindle nut of which, which is secured against rotation, the pump piston is coupled. The piston pump which is provided according to the invention can be designed as a compact unit. It advantageously possesses a cylinder body which comprises the measuring cylinder chamber and which, as the main body, is attached via a housing body, which is preferably cylindrical and which receives the transmission gear or the spindle gear, to a connection body for the attachment of the servomotor. The various components can advantageously be detachably connected to each other by screwed joints or the like. The aforementioned connection body, to which the servomotor can be joined by a flange, can form a housing for receiving a coupling device which couples the servomotor to the transmission gear or the spindle gear.

One quite particularly advantageous embodiment of the invention, which is of independent patentable importance in combination with a measuring apparatus for measuring the gas loading of a liquid, particularly a liquid plastics component, comprising a pump which is disposed in a circuit for the sample quantity and the pump piston of which can be adjusted, with displacement control and by means of an actuating drive, in both directions of travel in the measuring cylinder chamber, comprising a switchable valve device forming a filling and ejection valve for filling the measuring cylinder chamber with the sample quantity to be measured and for carrying away the sample quantity from the measuring cylinder chamber after the measuring operation has been performed, and comprising a pressure measuring device which is associated with the measuring cylinder chamber and with which the pressure of the sample quantity, which is isolated in the measuring cylinder chamber when the valve device is closed, can be measured at different predetermined positions of displacement of the pump piston in order to determine the gas loading, is obtained if an ultrasonic generator is associated with the measuring cylinder chamber of the measuring apparatus. By means of this ultrasonic generator, ultrasonic vibrations can be generated in the liquid sample which is accommodated in the measuring cylinder chamber whilst the pump piston is either moved in the measuring space in order to reduce the pressure or is held at the measuring pressure. The result of these ultrasonic vibrations is that the gas which is contained in the liquid is expelled considerably more rapidly than is possible solely by means of the reduced pressure which is generated. The time which is necessary to make an accurate measurement on a sample can thus be considerably reduced by means of the reduced pressure generator in combination with the ultrasonic generator. By the generation of ultrasonic waves in the sample, the time from introducing the sample quantity into the measuring cylinder until the instant at which a usable reading is obtained can in some cases be reduced to one quarter of the time which is necessary for a reliable measurement without ultrasound. Thus,the method according to the invention not only enables a particularly accurate determination of the gas loading to be made, but also enables this determination to be made very rapidly.

The inlet and the outlet for filling and emptying the measuring cylinder chamber advantageously lead radially into the latter at the side. The ultrasonic generator can then be disposed at one axial end of the measuring cylinder chamber, which results in a particularly compact arrangement and means that the ultrasonic generator is readily accessible. The latter is preferably replaceably accommodated in an opening in the measuring cylinder chamber, wherein in order to avoid direct contact between the liquid on which a measurement is to be made and the ultrasonic generator it may be advantageous if the opening is closed by a membrane. In this situation, however, it must be ensured that the vibrations generated by the ultrasonic generator are transmitted into the liquid unimpeded by the membrane. A particularly advantageous solution is achieved if the ultrasonic generator is accommodated in a holding flange and is secured thereto by means of fastening screws so that it can easily be replaced if this should become necessary, in the event of a malfunction,for example.

Instead of an ultrasonic wave generator, it is also possible to provide a different type of vibration generator, for example a rotating eccentric or the like, which generates vibrations of lower frequency at the piston pump, which vibrations are transmitted into the liquid sample and thus result in the more rapid expulsion of the gas from the liquid.

The measuring cylinder chamber can comprise at least one connection opening for a pressure and/or temperature sensor on its cylinder wall or on the cylinder body, by means of which sensor the pressures and temperatures in the individual measuring situations can be determined. A closable inspection and/or servicing opening to the measuring cylinder chamber can be provided in the cylinder wall, in order to provide a view into the measuring cylinder chamber through a sight glass or the like or to create an access for cleaning without the entire apparatus having to be completely dismantled.

The measuring apparatus according to the invention can be used particularly advantageously in a system, especially a plastics processing system, in which the measuring cylinder chamber of the piston pump is connected on its inlet side, via the filling valve, as directly as possible and in any event by a line which is as short as possible, to a vessel which contains the gas-laden liquid under an initial pressure and which is provided with a gas supply, and in which the measuring cylinder chamber of the piston pump is connected on its outlet side, via the ejection valve, to the return line to the supply vessel. The circuit for sample measurements can be capable of being shut off by means of an isolating valve from the system which is supplied with the gas-laden liquid from the supply vessel, so that the system pressure is not applied to the inlet side of the piston pump. Moreover, as is known in the art, the system advantageously comprises an evaluation and control device, which is connected via electrical signal and control lines to the measuring device which measures the pressure and which advantageously also measures the temperature of the test sample, and which is connected to the actuating drive and is also advantageously connected to a gas supply valve, which is disposed in a gas supply line leading to the supply vessel and by means of which the gas loading of the liquid situated in the supply vessel is adjusted to a constant set value.

Other features and advantages of the invention follow from the individual subsidiary claims and from the description given below of preferred examples of embodiments which are illustrated in the drawings.

BRIEF DESCRIPTION OF THE DRAWINGS

Reference may now be made to the drawings, which illustrate various embodiments that the invention may take in physical form and in certain parts and arrangements of parts wherein;

FIG. 2 is an axial section through a first embodiment of the piston pump shown in FIG. 1;

FIG. 3 is a cross-section along line III-III of FIG. 2;

FIG. 4 is a cross-section along line IV-IV of FIG. 2; and

DESCRIPTION OF PREFERRED EMBODIMENTS OF THE INVENTION

In order to provide an understanding of the invention, reference is made to the prior art documents cited in the introduction, the content of the disclosures of which is deemed to form part of the content of the present description of the invention.

Figure 1:
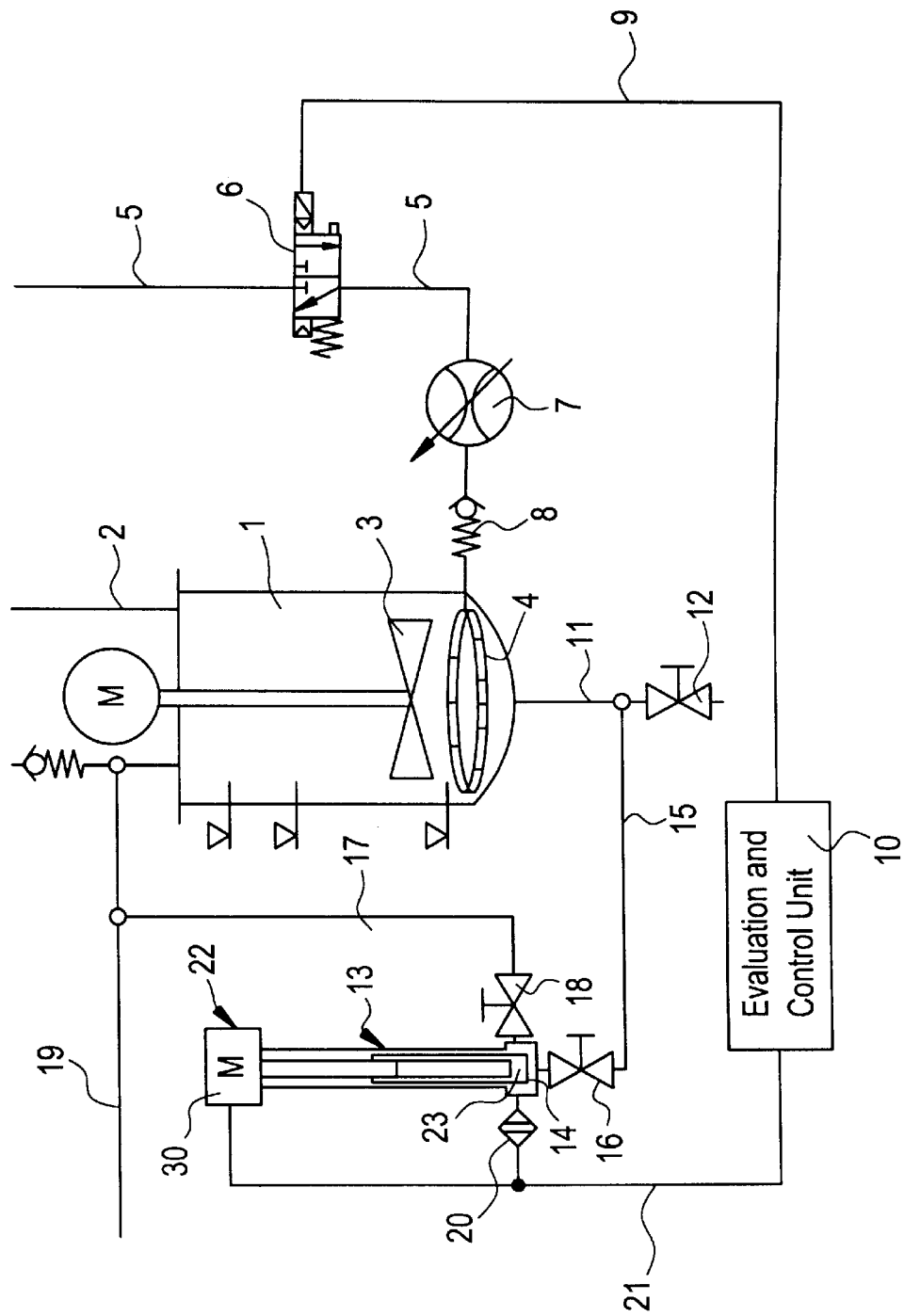
FIG. 1 illustrates a complete apparatus according to the invention together with the piston pump which is used for measuring the gas loading of the liquid and which is merely shown schematically here.

The operating system which is shown as a flow diagram in FIG. 1 is a component of a complete installation which is preferably used for plastics processing and which is used in particular here for the production of polyurethane foamed plastics. The system comprises a supply vessel 1 which receives a gas-laden liquid (plastics component), which is fed via a line 2 to the supply vessel and is held therein under a predetermined, constant initial pressure. In the supply vessel 1, as is known in the art, there is a stirrer 3 driven by a motor, below which there is an annular distributor 4 via which a gas, e.g. air, is introduced into the supply vessel and is finely distributed in the liquid situated therein, so that it is absorbed, predominantly at least, by the liquid. The distributor 4 is connected via a line 5 to a suitable source of gas for supplying the gas which serves to provide the gas loading of the liquid, wherein a gas supply valve 6, followed by a flow regulator 7 and a non-return valve 8, are disposed in the line 5. The gas supply valve 6 is constructed as a solenoid valve which can be actuated in its direction of opening by a central electrical evaluation and control unit 10 via an electrical control line 9, in order to connect the line 5 to the distributor 4 and to introduce the gas into the liquid situated in the supply vessel 1.

The supply vessel 1 is connected at its base to an outlet line 11 which leads to a mixer head, which is not illustrated, on the installation for plastics processing, in which the gas-laden component from the supply vessel 1 is mixed with a second plastics component before the reaction mixture is caused to foam. An isolating valve 12, is situated in the outlet line 11.

In order to adjust the gas loading of the liquid situated in the supply vessel 1 to a predetermined set value and to maintain it at this set value, a measuring apparatus is provided for measuring the gas loading of the liquid. This measuring apparatus has a piston pump 13 as its measuring device, the pump cylinder of which forms a measuring cylinder chamber 14 for receiving a sample quantity of the gas-laden liquid which is withdrawn from the supply vessel 1. The measuring cylinder chamber 14 is connected to the supply vessel 1, or in the embodiment illustrated to the outlet line 11 upstream of the isolating valve 12, via a feed line 15 in which a filling valve 16 is situated. It should be understood that the feed line 15, including the valve 16, is kept as short as possible, so that the sample on which the measurement is to be made is also in fact freshly withdrawn from the vessel 1 and has not previously stood in line 15 for an extended period.

The measuring cylinder chamber 14 of the piston pump 13 is also connected to the supply vessel 1 via a return line 17 in which an ejection valve 18 is situated, wherein in the embodiment illustrated the return line leads into a return line 19 which forms a return connection for excess, unmixed liquid from the aforementioned mixer head to the supply vessel 1. It can be seen that the piston pump 13 is disposed in a circuit which is formed by lines 15 and 17 and in which the supply vessel 1 is included, and which is isolated from the system pressure in the installation when the isolating valve 12 is closed. An arrangement is also possible, of course, in which the lines 15 and 17 forming the circuit are connected directly to the supply vessel 1 instead of to the lines 11 and 19, so that a measuring sample circuit which is independent of the system pressure is formed in this situation also.

As shown in FIG. 1, a measuring device 20 is associated with the measuring cylinder chamber 14 of the piston pump 13. This measuring device measures the different pressures of the gas-laden sample quantity which is present as a test sample in the measuring cylinder chamber 14 at different piston positions of the piston pump, and preferably also measures the temperature of the test sample during the measurement phase, wherein the pressure and temperature readings which are determined are fed via an electrical signal line 21 to the evaluation and control unit 10 for evaluation. The electrical signal line 21 is also employed for controlling the actuating drive 22 of the piston pump 13.

In order to measure the gas loading of the liquid situated in the supply vessel 1, the liquid is taken off at the vessel base, upstream of the isolating valve 12, via lines 11, 15 and is introduced into the measuring cylinder chamber 14 of the piston pump 13 via the open filling valve 16. In the course of this procedure, the pump piston 23 forming the measuring piston executes a suction stroke, and in the embodiment illustrated it therefore executes an upward stroke, whereby the volume of the measuring cylinder chamber 14 is correspondingly increased. As soon as the pump piston 23 has reached a first upper end position in the measuring cylinder chamber 14, at which the desired amount of sample is contained in the measuring cylinder chamber, the filling valve 16 is closed, so that with the ejection valve 18 closed at the same time the amount of sample drawn into the measuring cylinder chamber 14 is enclosed or isolated in the measuring cylinder chamber 14 in order to perform the measuring operation.

The gas loading of the sample is subsequently determined, for which purpose the pressure and temperature of the test sample are first measured by means of the measuring device 20, with the pump piston 23 at a standstill and with valves 16 and 18 closed, directly after the sample is introduced into the measuring chamber 14. The measured values which are thus determined are fed via the signal line 21 to the evaluation and control unit 10. The pump piston 23 is subsequently moved further in its reverse stroke direction (direction of suction) by a distance of travel and is held there so that the test sample enclosed in the measuring cylinder chamber 14 is subjected to a reduced pressure in order to effect forced separation of the gas and the liquid, namely the forced desorption of the gas from the liquid of the test sample. Thereafter, the pump piston 23 can then be moved back by a predetermined distance, i.e. in the direction of compression or in the sense of reducing the volume of the measuring cylinder chamber 14, for example so that a predetermined reference pressure (test pressure) e.g. atmospheric pressure is reached in the test sample, which is ascertained by a repeated pressure and temperature measurement by means of the measuring device 20, the measuring signals of which are likewise fed via the signal line 21 to the evaluation and control unit 10. Based on the gas law ($p \times V \times m \times R \times T$), the evaluation and control unit 10 can then calculate the amount of gas originally contained in the test sample via the pressure and temperature readings supplied to it and via the distances of travel of the pump piston 23, from which the changes in volume of the measuring cylinder chamber 14 are derived. If this amount of gas differs from a predetermined set value, the amount of gas in the liquid situated in the supply vessel 1 can be adjusted to the set value by supplying or removing gas via the evaluation and control unit 10 and the gas supply valve 6 controlled by it. After the measuring operation has been performed, the pump piston 23 is driven in the direction of compression (in a downward direction here) by the actuating drive 22, so that it returns the sample quantity contained in the measuring cylinder chamber 14 to the supply vessel 1 via the ejection valve 18, which is now open, and via the return line 17. It can be seen that the measurement of the gas loading of the liquid is made in a circulating operation, and is made by performing successive measuring operations until the test sample withdrawn from the supply vessel 1 in the measuring cylinder chamber 14 of the piston pump 13 corresponds to the same condition (gas loading) as that which is predetermined by the set value.

The construction of the piston pump 13 is explained in more detail below with reference to FIGS. 2 to 5. It can be seen that the embodiment of the piston pump 13 which is shown in FIGS. 2-4 comprises a cylinder body 24 which consists of a metal block, which comprises the measuring cylinder chamber 14 as a cylinder bore, and in which the pump piston 23 is guided with a piston seal, wherein at one end the measuring cylinder chamber 14 comprises the inlet 25 for the sample quantity which is supplied via the feed line 15 (FIG. 1) and the filling valve 16, and at right angles thereto comprises the outlet 26 for the connection of the return line 17 to the ejection valve 18 which is situated here. A cylindrical housing body 27, which receives a transmission gear in the form of a spindle gear which is connected to the piston 23, is screwed to the cylinder body 24 at its opposite end to the inlet 25. At its other housing end, the housing body 27 is detachably connected, by a flange plate 28 which can be screwed on, to a connection body 29, at the free end of which a servomotor 30 of the actuating drive 22 is detachably mounted. The motor shaft 31 of the actuating drive 22 is coupled as a drive to the transmission gear or to the displacement spindle 33 thereof via a coupling 32 in the interior of the connection body 29, wherein the coupling 32 is constructed here as an insertion coupling. The displacement spindle 33 is rotatably mounted on the connection body 29 by a rolling bearing 34, in a bearing bush 35 which is secured by means of the flange plate 28 and to which the cylindrical housing body 27 is screwed at one end. The servomotor consists of an electric stepper motor, the direction of rotation of which can be reversed, and which is capable of driving the displacement spindle 33 in both directions of rotation in order to move the pump piston 23 in both directions of travel. A spindle nut 36, to which the pump piston 23 is coupled in the manner of a drive, is seated on the external thread of the displacement spindle 33 in the interior of the housing body 27.

As shown in FIG. 2, the piston 23 has a piston shank 37 of reduced diameter, on which it is provided with a sliding bearing 38 by means of which it is guided so that it is axially displaceable in the cylindrical housing part 27. The piston shank is adjoined by a hollow piston attachment 39, which is also axially guided in the housing body 27 and into which the piston end of the displacement spindle 33 leads which is attached thereto. A rotational lock in the form of a radially protruding pin 41 is fixedly disposed on the hollow piston attachment 39, radially thereto. The rotational lock can also consist of a screwed-in stud, and passes through an axial slotted opening 42 in the housing body 27, so that when the displacement spindle 33 is driven the pump piston 23 and the spindle nut 36 attached thereto are locked against rotation, and the spindle nut 36 together with the pump piston 23 can therefore only execute an axial stroke movement in the directions of suction and compression of the pump piston.

The piston pump 13 which is illustrated as an embodiment in FIG. 2 also comprises sensors which determine the piston stroke in both directions of travel. These sensors consist of proximity switches 43 and 44, by means of which the actuating drive or the servomotor 30 can be switched on and off and the direction of rotation thereof can be reversed. The proximity switches are disposed at an axial spacing from each other on the housing body 27, in the end regions of the slotted opening 42 thereof, and can be acted upon by the pin. During the suction phase of the test sample, during the measurement thereof in the measuring cylinder chamber 14 and during the ejection of the test sample after the measuring operation is complete, the proximity switches 43 and 44 limit the stroke movements of the pump piston 23 via the actuating drive thereof. Stroke travel measuring devices such as this for the measuring pistons of measuring cylinders are known in multiple forms for the measurement of the gas loading of liquids, so that a further description thereof is unnecessary in this respect.

Figure 5:
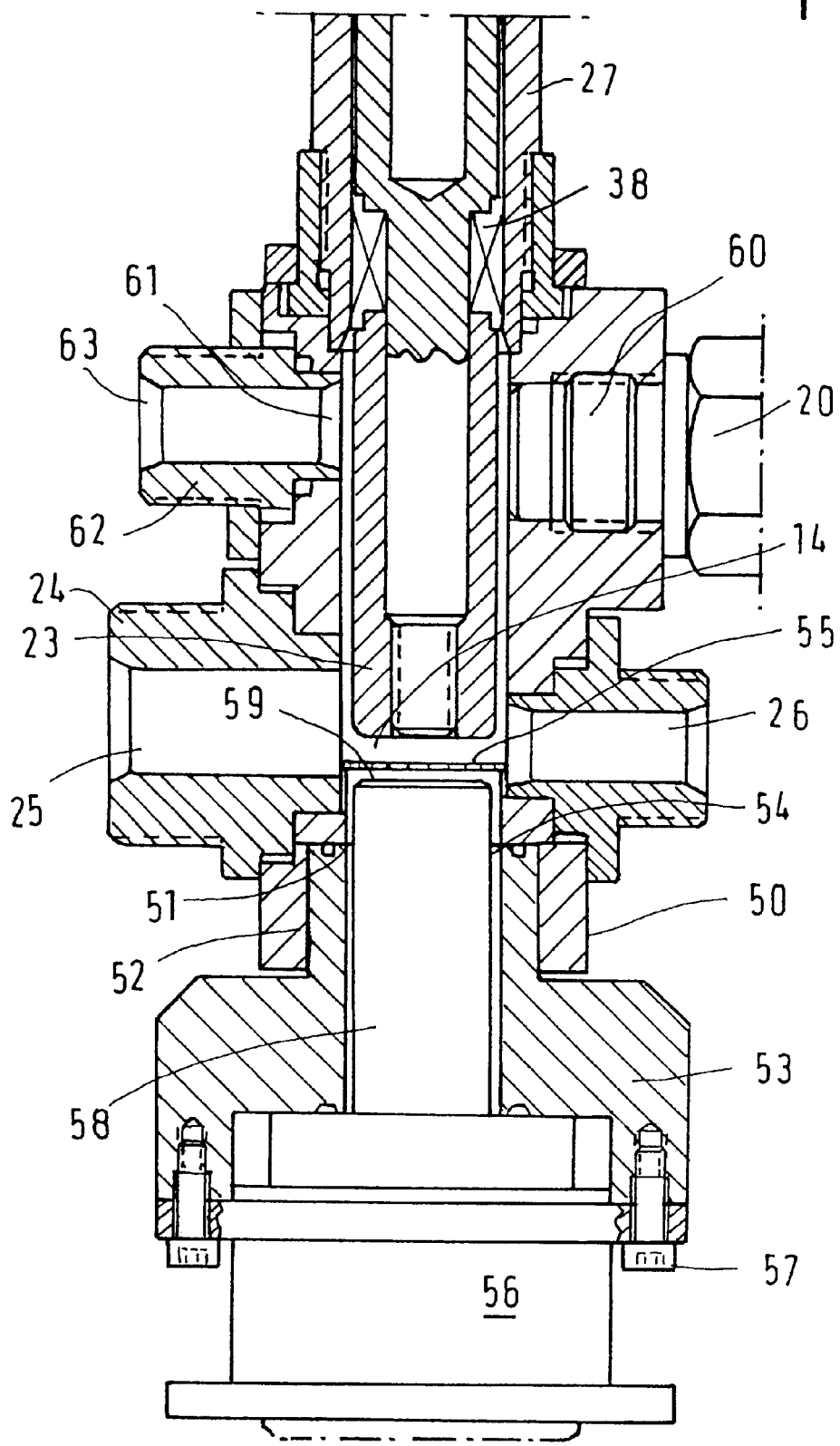
FIG. 5 shows a second, preferred embodiment of the piston pump as an illustration which corresponds to that of FIG. 2 but in which one portion only is reproduced on an enlarged scale.

FIG. 5 shows the lower end section, which comprises the measuring cylinder chamber 14, of a second, particularly preferred embodiment of the piston pump according to the invention. The construction of the upper region thereof, which is not illustrated, corresponds to the upper region of the arrangement shown in FIG. 2, so that a detailed description of this region can be omitted.

In the second embodiment which is illustrated in FIG. 5, both the inlet 25 and the outlet 26 for the liquid sample are constructed as connections which are aligned radially in relation to the cylinder chamber 14 and via which the sample quantity is introduced into the measuring cylinder chamber 14 and is ejected again after the measurement has been made. An axial bore 51 with an internal thread 52, into which a holding flange 53 is screwed, is provided at the axial (lower) end 50 of the measuring cylinder chamber 14 in the cylinder body 24. The holding flange 53 has a central bore, which together with the bore 51 forms a cylindrical passageway 54 to the measuring chamber 14 which can be closed by a membrane 55 at its front end which points towards the pump piston 23 at the base of the measuring cylinder chamber 14.

The holding flange 53 bears an ultrasonic generator 56, which is screwed to the flange by fastening screws 57 for this purpose. The ultrasonic generator is a commercially available component and has a cylindrical ultrasonic wave transmitter 58 at its front end 59 which points towards the pump piston and is inserted in the axial passageway 54 with its end face in contact with the membrane 55.

By means of the ultrasonic generator, the liquid sample which is accommodated in the measuring cylinder chamber 14 can be acoustically irradiated with ultrasonic waves, whereby the desorption process, namely the separation of the liquid from the gas dissolved therein, can be considerably speeded up compared with the first embodiment illustrated in FIG. 2. The ultrasonic waves which are introduced from the ultrasonic generator 58 via the membrane 55 into the liquid therefore result in a more rapid expulsion of the gas than that which is possible solely due to the reduced pressure which is created by the movement of the piston. It has been shown that the time for which the reduced pressure has to be exerted on the liquid sample for desorption in order to obtain correct test results can be reduced by 50% or more if the sample is simultaneously acted upon by ultrasound. The reduction in this time of measurement is particularly advantageous because the test result is obtained considerably nearer the time at which the test sample was actually withdrawn from the vessel. The shorter is the period between taking the test sample and obtaining the test result, the more rapidly and accurately the gas content in the liquid can be controlled at the desired set value.

In the embodiment of the piston pump which is illustrated in FIG. 5, a connection opening 60 for a temperature and pressure sensor 20 can be seen above the outlet 26 in the cylinder body 24, and is situated radially in relation to an inspection and servicing opening 61 which is also disposed in the cylinder body 24. In operation, this inspection and servicing opening is closed in an air-tight manner by means of a screwed-in eyepiece 62, wherein the behavior of the liquid to be measured in the measuring cylinder chamber 14 during the measurement can be observed through the sight glass 63 screwed into the eyepiece. For servicing purposes, for cleaning for example, the eyepiece 62 can be unscrewed from the opening 61 in order to connect a hose for flushing liquid or the like.

It can be seen that the measuring apparatus which was described in connection with FIGS. 2 to 5, and which substantially consists of the piston pump, is of very compact construction, and that it is possible to execute very exact stroke movements, in both directions of travel, of the pump piston 23 which forms the measuring piston, via the transmission gear which is constructed as a spindle gear, so that, via the measured values which are measured by the measuring device 20, it is possible to obtain a very accurate measurement of the gas loading of the test sample which is isolated in the measuring cylinder chamber 14 during the measuring operation. A measurement can also be made on the test sample by more than two different positions of displacement of the pump piston 23 in the measuring cylinder chamber 14.

Via the physical quantities comprising the overpressure and reduced pressure on the test sample, and via the measured pressure and temperature values which are determined thereby, as well as the changes in volume which are due to the stroke travel of the pump piston, measurements can effectively be made, based on the gas law, of gases which are dissolved and which exist freely in liquids of any viscosity, wherein the measured values which are determined can be used to adjust the gas loading of liquids, as is the case for the installation shown in FIG. 1, for example.

The invention has been described with reference to preferred and alternate embodiments. Modifications and alterations will become apparent to those skilled in the art upon reading and understanding the detailed discussion of the invention provided herein. This invention is intended to include all such modifications and alterations insofar as they come within the scope of the present invention.

What is claimed is:

1. A measuring apparatus for measuring gas loading of a liquid plastics component in a system, comprising a piston pump which is disposed in a circuit for a sample quantity obtained from said system and a piston of said piston pump of which can be adjusted, with displacement control and by means of an actuating drive, in both directions of travel in a measuring cylinder chamber; a switchable valve device forming a filling and ejection valve to fill said measuring cylinder chamber with said sample quantity to be measured and for carrying away said sample quantity from said measuring cylinder chamber after a measuring operation has been performed; and a pressure measuring device which is associated with said measuring cylinder chamber and with which a pressure of said sample quantity, which is isolated in said measuring cylinder chamber when said switchable valve device is closed, can be measured at different predetermined positions of displacement of said piston in order to determine said gas loading, an actuating drive of said piston pump including a servomotor having a transmission gear and said piston pump also a feed pump which returns said sample quantity from said measuring cylinder chamber to said system after said measuring operation has been performed.

2. The measuring apparatus of claim 1, wherein said filling valve and said ejection valve of said valve device includes valves which can be switched independently of each other between a closed position and an open position.

3. The measuring apparatus of claim 1, wherein said servomotor includes an electric torque motor, the direction of rotation of which can be reversed.

4. The measuring apparatus of claim 1, wherein sensors are provided which determine said piston travel in both directions of travel.

5. The measuring apparatus of claim 4, wherein said sensors include proximity switches which control said actuating drive.

6. The measuring apparatus of claim 1, wherein said inlet side of said measuring cylinder chamber of said piston pump is connected via said filling valve to a supply vessel which contains said gas-laden liquid under an initial pressure and which is provided with a gas supply, and on said outlet side is connected via said ejection valve to a return line to said supply vessel.

7. The measuring apparatus of claim 6, wherein said circuit for sample measurement can be shut off via at least one valve from said system which is supplied with said gas-laden liquid from said supply vessel.

8. The measuring apparatus of claim 1, wherein an evaluation and control unit is provided which is connected via electrical signal and control lines to said pressure measuring device and to an actuating drive of said piston pump, and is also connected to a gas supply valve which is disposed in a gas supply line leading to said system.

9. The measuring apparatus of claim 1, wherein said pressure measuring device which is associated with said piston pump includes a combined pressure and temperature measuring device.

10. The measuring apparatus of claim 1, including an ultrasonic generator associated with said measuring cylinder chamber.

11. The measuring apparatus of claim 1, wherein an inlet and an outlet for filling and emptying lead radially into said measuring cylinder chamber at the side thereof.

12. The measuring apparatus according to claim 10, wherein said ultrasonic generator is disposed at an axial end of said measuring cylinder chamber.

13. The measuring apparatus of claim 10, wherein said ultrasonic generator is replaceably mounted in an opening on said measuring cylinder chamber.

14. The measuring apparatus of claim 13, wherein said opening on said measuring cylinder chamber is closed by a membrane.

15. The measuring apparatus of claim 10, wherein said ultrasonic generator is mounted in a holding flange and is secured thereto by means of fastening screws.

16. The measuring apparatus of claim 1, wherein said measuring cylinder chamber has at least one connection opening for a pressure sensor.

17. A measuring apparatus for measuring gas loading of a liquid plastics component in a system, comprising a piston pump which is disposed in a circuit for a sample quantity obtained from said system and a piston of said piston pump of which can be adjusted, with displacement control and by means of an actuating drive, in both directions of travel in a measuring cylinder chamber; a switchable valve device forming a filling and ejection valve to fill said measuring cylinder chamber with said sample quantity to be measured and for carrying away said sample quantity from said measuring cylinder chamber after a measuring operation has been performed; and a pressure measuring device which is associated with said measuring cylinder chamber and with which a pressure of said sample quantity, which is isolated in said measuring cylinder chamber when said switchable valve device is closed, can be measured at different predetermined positions of displacement of said piston in order to determine said gas loading, an actuating drive of said piston pump including a servomotor having a transmission gear and said piston pump also a feed pump which returns said sample quantity from said measuring cylinder chamber to said system after said measuring operation has been performed, said transmission gear includes a spindle gear, said piston, and a spindle nut attached thereto and secured against rotation.

18. The measuring apparatus of claim 17, wherein said piston pump has a hollow piston attachment on a drive side of said piston pump which receives a displacement spindle with the spindle nut.

19. The measuring apparatus of claim 18, wherein said rotational locking for said spindle nut and said piston includes a pin which is fixed radially to said hollow piston attachment and which is led into an axial slot in a housing body.

20. A measuring apparatus for measuring gas loading of a liquid plastics component in a system, comprising a piston pump which is disposed in a circuit for a sample quantity obtained from said system and a piston of said piston pump of which can be adjusted, with displacement control and by means of an actuating drive, in both directions of travel in a measuring cylinder chamber; a switchable valve device forming a filling and ejection valve to fill said measuring cylinder chamber with said sample quantity to be measured and for carrying away said sample quantity from said measuring cylinder chamber after a measuring operation has been performed; and a pressure measuring device which is associated with said measuring cylinder chamber and with which a pressure of said sample quantity, which is isolated in said measuring cylinder chamber when said switchable valve device is closed, can be measured at different predetermined positions of displacement of said piston in order to determine said gas loading, an actuating drive of said piston pump including a servomotor having a transmission gear and said piston pump also a feed pump which returns said sample quantity from said measuring cylinder chamber to said system after said measuring operation has been performed, said piston pump includes a cylinder body which comprises said measuring cylinder chamber and which is attached, via a housing body which receives said transmission gear, to a connection body for the attachment of said servomotor.

21. The measuring apparatus of claim 1, wherein said housing body is detachably connected to said cylinder body and said connection body.

22. The measuring apparatus of claim 1, including a coupling device for coupling said servomotor to said transmission gear being disposed in said connection body.

23. A measuring apparatus for measuring gas loading of a liquid plastics component in a system, comprising a piston pump which is disposed in a circuit for a sample quantity obtained from said system and a piston of said piston pump of which can be adjusted, with displacement control and by means of an actuating drive, in both directions of travel in a measuring cylinder chamber; a switchable valve device forming a filling and ejection valve to fill said measuring cylinder chamber with said sample quantity to be measured and for carrying away said sample quantity from said measuring cylinder chamber after a measuring operation has been performed; and a pressure measuring device which is associated with said measuring cylinder chamber and with which a pressure of said sample quantity, which is isolated in said measuring cylinder chamber when said switchable valve device is closed, can be measured at different predetermined positions of displacement of said piston in order to determine said gas loading, an actuating drive of said piston pump including a servomotor having a transmission gear and said piston pump also a feed pump which returns said sample quantity from said measuring cylinder chamber to said system after said measuring operation has been performed, said measuring cylinder including a closable inspection opening in a cylinder wall.

24. A method of determining gas loading of a liquid, comprising taking a sample quantity from a liquid circuit and introducing said sample quantity into a measuring cylinder chamber of a measuring apparatus constructed as a piston pump, measuring an initial pressure of said sample quantity after closing a filling valve and an ejection valve of said piston pump, measuring an initial pressure in said measuring cylinder chamber by displacing said piston pump and desorbing gas contained in said sample quantity, accelerating desorption of said gas in said sample quantity by subjecting said sample quantity to ultrasonic waves, measuring pressure in said measuring cylinder chamber a second time to obtain a second pressure, comparing said second pressure to said initial pressure, determining an amount of gas after said desorption of said sample quantity, and subsequently ejecting said sample quantity into said liquid circuit after opening said ejection valve.

25. The method of claim 24, including measuring an initial temperature of said sample quantity during said measuring of said initial pressure, measuring a second temperature during said measuring of said second pressure and comparing said initial temperature to said second temperature to determine said amount of gas after said desorption of said sample quantity.

26. A measuring apparatus for measuring gas loading of a liquid plastics component in a system, comprising a piston pump which is disposed in a circuit for a sample quantity and a piston of said piston pump of which can be adjusted, with displacement control and by means of an actuating drive, in both directions of travel in a measuring cylinder chamber, comprising a switchable valve device forming a filling and an ejection valve for filling said measuring cylinder chamber with said sample quantity to be measured and for carrying away said sample quantity from said measuring cylinder chamber after a measuring operation has been performed, and comprising a temperature measuring device which is associated with said measuring cylinder chamber and with which a temperature of said sample quantity, which is isolated in said measuring cylinder chamber when said valve device is closed, can be measured at different predetermined positions of displacement of said piston in order to determine said gas loading, an actuating drive of said piston pump including a servomotor having a transmission gear and said piston pump being a feed pump which returns said sample quantity from said measuring cylinder chamber to said system after said measuring operation has been performed.

27. A measuring apparatus for measuring gas loading of a liquid component in a chemical reaction system comprising a measuring chamber that can be isolated from said chemical reaction system; at least one valve to allow a sample liquid from said system to be introduced into and be expelled from said measuring chamber and to isolate said sample liquid in said measuring chamber from said system; a piston pump including a piston that is displaceable in said measuring chamber to controllably reduce and increase the volume of said measuring chamber; a measuring device associated with said measuring chamber to measure at least one physical parameter when said sample liquid is in said measuring chamber and isolated from said system; and a gas separation accelerator; at least one of said physical parameters including a parameter selected from the group consisting of volume of said measuring chamber, volume of said sample liquid in said measuring chamber, temperature in said measuring chamber, piston position in said measuring chamber, and combinations thereof; said piston pump being a loading pump to load said sample liquid in said measuring chamber and an expelling pump to expel said sample liquid from said measuring chamber after measuring said gas loading of said sample liquid.

28. The measuring apparatus as defined in claim 27, wherein said piston pump causes said sample liquid to load into said measuring chamber by controllably retracting said piston to cause an increase of volume in said measuring chamber.

29. The measuring apparatus as defined in claim 27, wherein said piston pump causes said sample liquid to be expelled from said measuring chamber by controllably advancing said piston to cause a decrease of volume in said measuring chamber.

30. The measuring apparatus as defined in claim 28, wherein said piston pump causes said sample liquid to be expelled from said measuring chamber by controllably advancing said piston to cause a decrease of volume in said measuring chamber.

31. The measuring apparatus as defined in claim 27, wherein said piston pump controllably moves said piston in said measuring chamber while said sample liquid is in said measuring chamber and isolated from said system to cause at least one of said physical parameters to change in order to determine said gas loading of said sample liquid.

32. The measuring apparatus as defined in claims 27, wherein said gas separation accelerator includes an ultrasonic generator connected to said measuring chamber.

33. The measuring apparatus as defined in claim 27, including an evaluation and control unit to control the operation of said piston pump and to calculate the gas loading of said sample liquid upon receiving a plurality of said measured physical parameters from said measuring device.

34. A measuring apparatus for measuring gas loading of a liquid component in a chemical reaction system comprising a measuring chamber that can be isolated from said chemical reaction system; at least one valve to allow a sample liquid from said system to be introduced into and be expelled from said measuring chamber and to isolate said sample liquid in said measuring chamber from said system; a piston pump including a piston that is displaceable in said measuring chamber to controllably reduce and increase the volume of said measuring chamber; a measuring device associated with said measuring chamber to measure at least one physical parameter when said sample liquid is in said measuring chamber and isolated from said system; and a gas separation accelerator; at least one of said physical parameters including a parameter selected from the group consisting of volume of said measuring chamber, volume of said sample liquid in said measuring chamber, temperature in said measuring chamber, piston position in said measuring chamber, and combinations thereof; said piston pump being a loading pump to load said sample liquid in said measuring chamber and an expelling pump to expel said sample liquid from said measuring chamber after measuring said gas loading of said sample liquid, said piston pump causing said sample liquid to load into said measuring chamber by controllably retracting said piston to cause an increase of volume in said measuring chamber, said piston pump causing said sample liquid to be expelled from said measuring chamber by controllably advancing said piston to cause a decrease of volume in said measuring chamber, said piston pump controllably moving said piston in said measuring chamber while said sample liquid is in said measuring chamber and isolated from said system to cause at least one of said physical parameters to change in order to determine said gas loading of said sample liquid.

35. The measuring apparatus as defined in claim 34, wherein said gas separation accelerator includes an ultrasonic generator connected to said measuring chamber.

36. The measuring apparatus as defined in claim 35, including an evaluation and control unit to control the operation of said piston pump and to calculate the gas loading of said sample liquid upon receiving a plurality of said measured physical parameters from said measuring device.

* * * * *